United States Patent [19]

Hisazumi et al.

[11] Patent Number: 4,676,231
[45] Date of Patent: Jun. 30, 1987

[54] LASER PROBE

[75] Inventors: Haruo Hisazumi, Kanazawa; Norio Miyoshi, Fukui, both of Japan

[73] Assignee: Olympus Optical Co., Ltd., Tokyo, Japan

[21] Appl. No.: 773,968

[22] Filed: Sep. 9, 1985

[30] Foreign Application Priority Data

Sep. 14, 1984 [JP] Japan .................. 59-193305

[51] Int. Cl.⁴ .................................................. A61B 1/06
[52] U.S. Cl. ........................................ 128/6; 128/303.1
[58] Field of Search ...................................... 128/4-6, 128/303.1, 395–398; 350/96.18, 96.24, 96.26, 128, 129; 362/318, 355, 356

[56] References Cited

U.S. PATENT DOCUMENTS

| 3,724,383 | 4/1973 | Gallaghan et al. | 350/96.18 |
| 3,799,150 | 3/1974 | Bonnet | 128/6 |
| 3,809,072 | 5/1974 | Ersek et al. | 128/397 |
| 4,170,035 | 10/1979 | Walker | 362/318 |
| 4,201,199 | 5/1980 | Smith | 128/6 |
| 4,233,493 | 11/1980 | Nath | 128/397 |
| 4,257,672 | 3/1981 | Balliet | 350/96.18 |
| 4,327,963 | 5/1982 | Khoe et al. | 350/96.18 |
| 4,470,407 | 9/1984 | Hussein | 128/6 |

FOREIGN PATENT DOCUMENTS

| 3119322 | 1/1983 | Fed. Rep. of Germany . |
| 3323365 | 3/1984 | Fed. Rep. of Germany . |
| 0810205 | 3/1981 | U.S.S.R. ............................ 128/6 |

Primary Examiner—William E. Kamm
Assistant Examiner—Max F. Hindenburg
Attorney, Agent, or Firm—Armstrong, Nikaido, Marmelstein & Kubovcik

[57] ABSTRACT

This invention is a laser probe made to cure and extinguish within a short time surface-existing tumors generated in a wide range within a body cavity and having a substantially spherical hollow light diffusing part enclosing a light dispersing medium at the tip, light leading fibers inserted in this light diffusing part and a laser light emitting end arranged substantially in the center of the light diffusing part. This laser probe diffuses a laser light emitted from the emitting end of the light leading fibers over a wide range from the light diffusing part to illuminate the objects with a uniform intensity.

4 Claims, 7 Drawing Figures

FIG.4
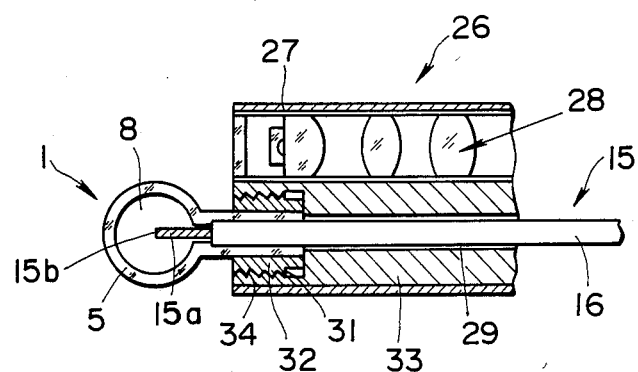
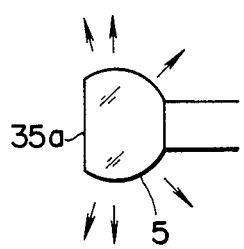
FIG.5(A)
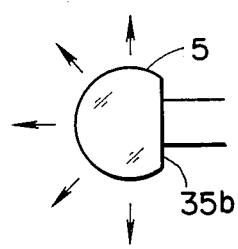
FIG.5(B)
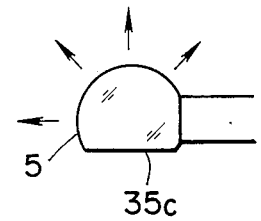
FIG.5(C)

LASER PROBE

BACKGROUND OF THE INVENTION

1. Field of the Invention:

This invention relates to a laser probe radiating a laser light toward tumors generated within a body cavity in order to extinguish the tumors.

2. Related Art Statement

There is recently practiced a curing method wherein a hematopolphyllin derivative (HPD) is taken into tumors by oral administration, a laser light is radiated there and the tumors are extinguished by a photochemical reaction. The fiber end of the laser probe is tapered or made spherical as a means of diffusing and radiating a laser light onto tumors. However, the laser light can be diffused only in an angle up to about 30 degrees today.

With such conventional laser probe of a narrow emitting angle, in the case of curing surface-existing tumors generated in a wide range within a body cavity, it will be necessary to radiate the laser light in turn onto the tumors in the wide range and, therefore, there is a problem that a long time is required to radiate the laser light.

By the way, in the gazette of West German laid open patent No. 3119322, there is disclosed a probe wherein, in order to coagulate the esphagus varix with heat, a fiber tip part as an emitting end surface is roughened and exposed and is covered with a cap formed of a light passing material and the air layer existing within the cap is used as a heat transmitter. However, its object is not to diffuse the laser light but is to coagulate the varix with heat by keeping the probe in close contact with the varix. Also, in the gazette of West German laid open patent No. 3323365, it is disclosed to illuminate and treat a body cavity by dispersing a light by using a dispersing medium. However, the above mentioned dispersing medium is put in the body cavity itself or a balloon and therefore can not radiate the light with a uniform intensity.

OBJECTS AND SUMMARY OF THE INVENTION

An object of the present invention is to provide a laser probe made to cure and extinguish within a short time surface-existing tumors generated in a wide range within a body cavity by diffusing and radiating a laser light in a very wide range and with a uniform intensity.

Another object of the present invention is to provide a laser probe wherein the light diffusing part is made removable so that it may be easy to replace the light diffusing part and the enclosed light dispersing medium.

Another further object of the present invention is to provide a laser probe which can be inserted into a body cavity through a sheath inserted into the body cavity.

Further, another object of the present invention is to provide a laser probe which can be inserted into a body cavity through a treating tool channel of an endoscope.

Another further object of the present invention is to provide a laser probe wherein the light diffusing part can be fitted to the tip of a treating tool channel of an endoscope.

Briefly, the present invention has a substantially spherical hollow light diffusing part enclosing a light dispersing medium at the tip and a laser light emitting end of light leading fibers inserted from the hand gripping side arranged substantially in the center within the light diffusing part so that, when the incident end of the above mentioned light leading fibers is connected to a laser oscillator and a laser light is radiated, the laser light emitted from the above mentioned emitting end of the light leading fibers will be dispersed by the light dispersing medium so as to be diffused and radiated over a wide range from the substantially spherical hollow light diffusing part and, on the other hand, as the emitting end is positioned substantially in the center of the light diffusing part, the diffused and radiated laser light will be radiated with a more uniform intensity.

These and other objects and advantages of the present invention will become more apparent from the following detailed description.

BRIEF DESCRIPTION OF THE DRAWINGS

FIG. 1 is a sectioned view.

FIG. 2 is a sectioned view showing a using example.

FIG. 4 is a sectioned view of the third embodiment of the present invention.

FIGS. 5(A), (B) and (C) are side views showing light diffusing parts of the fourth embodiment of the present invention.

DETAILED DESCRIPTION

Figure 1:
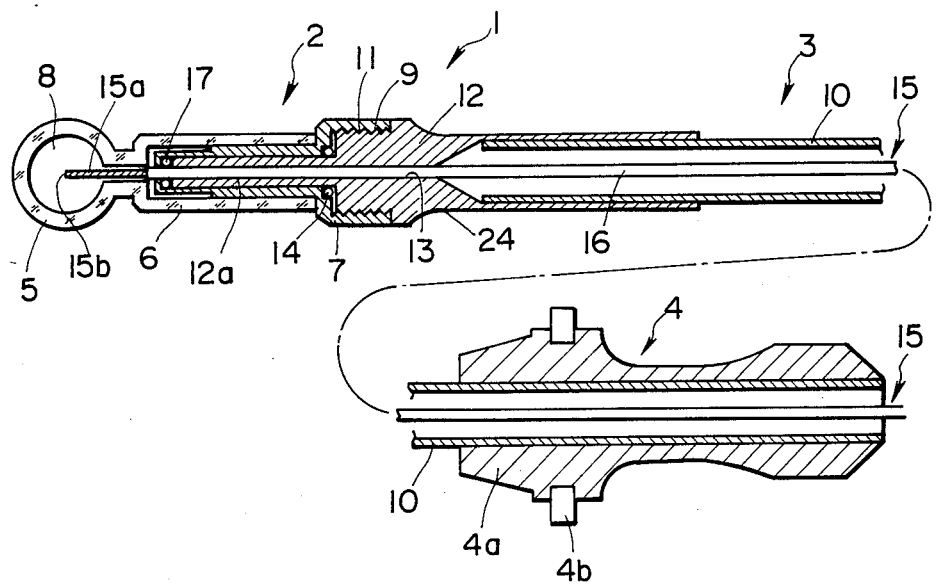
FIGS. 1 and 2 relate to the first embodiment of the present invention.
Figure 2:
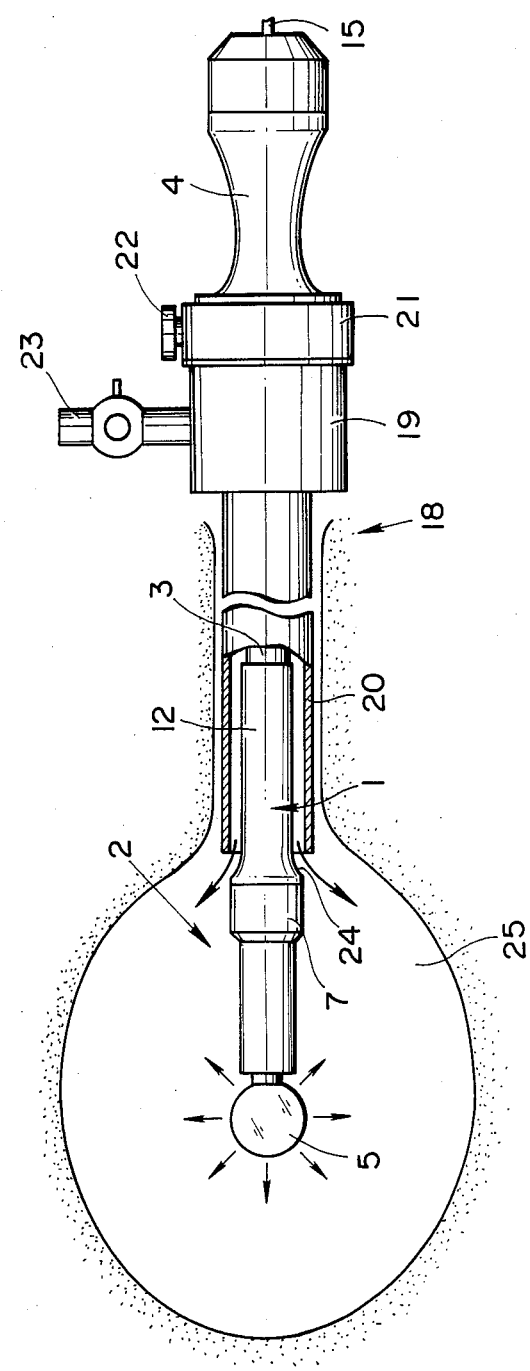

The first embodiment of the present invention is shown in FIGS. 1 and 2.

As shown in FIG. 1, a laser probe 1 is formed of a tip part 2, intermediate part 3 and hand gripping part 4. The tip part 2 has at the most forward tip a light diffusing part 5 formed to be spherical hollow of such light passing material as glass or transparent plastic. This light diffusing part 5 has a long cylindrical neck part 6 fitted and secured to a holding member 7 formed to be cylindrical. A light dispersing medium 8 dispersing a laser light in a wide range is enclosed within the light diffusing part 5. For this light dispersing medium 8, a granular medium of a fixed concentration of a granule diameter less than one micron is adapted to uniformly diffuse the light and, for example, Intralipos (trade name of Green Cross Company, Ltd. of a nutrient containing fine grains of fat) of a concentration of 2.5% is used. The base part of the above mentioned holding member 7 is expanded in the diameter and a female screw 9 is formed on the inner periphery of this expanded diameter part and is screwed and connected with a tip mouthpiece 12 having a male screw 11 on the outer periphery and secured to the tip of an elongated hollow shaft body 10 forming the intermediate part 3. This tip mouthpiece 12 has a through hole 13 in the axial direction and has at the tip a cylindrical part 12a of a fine diameter projected and inserted to the tip of the cylindrical holding member 7. Such sealing member 14 as an O-ring to prevent water from coming in from outside is fitted between the above mentioned tip mouthpiece 12 and the inner periphery of the holding member 7. The elongated hollow shaft body 10 forming the above mentioned intermediate part 3 and consisting of a soft or hard pipe or closely wound coil is inserted in and connected with the hand gripping part 4 in the base part, is extended and opened at the rear end of the hand gripping part 4 and is connected to a laser oscillator not illustrated from the opening of this hand gripping part 4 and light leading fibers 15 transmitting a laser light into the above mentioned light diffusing part 5 are inserted through the hollow shaft body 10. These light leading fibers 15 have a coating member 16 on the outer periphery, are inserted into the most forward light diffusing part 5 through the hollow shaft body 10, tip mouthpiece 12 and holding member 7, have no coating member 16 within the light diffusing part 5 and expose light leading fibers 15a. The laser light emitting end 15b of the light leading fibers 15a is arranged in the center position of the spherical hollow light diffusing part 5 so as to diffuse and radiate the laser light from the light diffusing part 5 at a uniform intensity. Such sealing member 17 as an O-ring is fitted between the light leading fibers 15 having the coating member 16 and the inner periphery of the tip of the holding member 7 so that the light dispersing medium 8 enclosed within the light diffusing part 5 may not leak out.

As a using example, the laser probe 1 of the above mentioned formation is inserted in combination with a sheath 18 into a body cavity. Such sheath 18 is known and consists of a hand gripping part body 19 and an elongated inserted part 20 extended out to the tip side. The intermediate part 3 of the laser probe 1 is inserted into the inserted part 20, the tip part 2 is projected and the fixing part 4a side of the hand gripping part 4 is fitted to the hand gripping part body 19 to be assembled. Therefore, the fixing part 4a of the hand gripping part 4 has a connecting member 4b provided to project on the outer periphery and this connecting member 4b is locked in a locking groove not illustrated formed on the inner periphery of the hand gripping part body 19 of the sheath so as to be connected. On the other hand, the hand gripping part body 19 of the sheath 18 has a removable member 21 and removable button 22. Further, the hand gripping part body 19 of the sheath 18 has a water feeding port 23 with a cock for feeding water into a body cavity. Further, in the tip part 2 of the laser probe 1, the outer periphery near the projecting part of the inserted part 20 of the sheath 18 is cut to form a recess 24 so that the above mentioned fed water amount may be larger.

In such formation, the laser probe 1 of the present invention is combined with the sheath 18 inserted into the body cavity 25, the laser probe 1 is inserted in the tip part 2 into the body cavity 25 and the spherical hollow light diffusing part 5 is positioned and set substantially in the center of the body cavity 25. By the way, an irrigating liquid or gas is fed into the body cavity 25 through the water feeding port 23 of the sheath 18 to inflate the body cavity 25 so that a distance between the light diffusing part 5 of the laser probe 2 and the inner wall of the body cavity may be taken. In such state, the incident end part of the light leading fibers 15 is connected to a laser oscillator to radiate a laser light. The laser light emitted from the emitting end 15b of the light leading fibers 15 will be dispersed by the light dispersing medium 8 of a fixed concentration within the spherical hollow light diffusing part 5 and will be diffused and radiated at a uniform intensity from the light diffusing part 5. As this light diffusing part 5 is formed to be spherical hollow and the laser light emitting end 15b is arranged in the light diffusing part, the laser light will be radiated at a uniform intensity over the entire range of substantially 360 degrees and therefore all of surface-existing tumors generated over a wide range within a body cavity having taken in, for example, a hematopolphyllin derivative by oral administration in advance can be simultaneously illuminated so that, with the radiation of a laser light within a very short time, tumors may be cured and extinguished. By the way, the position within the body cavity 25 of the spherical hollow light diffusing part 5 of the above mentioned laser probe 1 can be freely set, for example, by an ultrasonic wave diagnosing apparatus from outside the body.

Thus, by positioning the spherical hollow light diffusing part 5 of the laser probe 1 of the present invention substantially in the center of a body cavity, without scanning the light diffusing part 5 within the body cavity, a laser light can be radiated at a uniform intensity over the entire body cavity and tumors can be cured by the laser light radiation within a short time. The light diffusing part 5 in the tip part 2 of the laser probe 1 can be fitted and removed by the screw and therefore the light diffusing part 5 and the enclosed light dispersing medium 8 can be easily replaced. Further, the laser probe 1 can be used as combined with the existing sheath 18 and therefore can be safely, positively and easily inserted into a body cavity.

Figure 3:
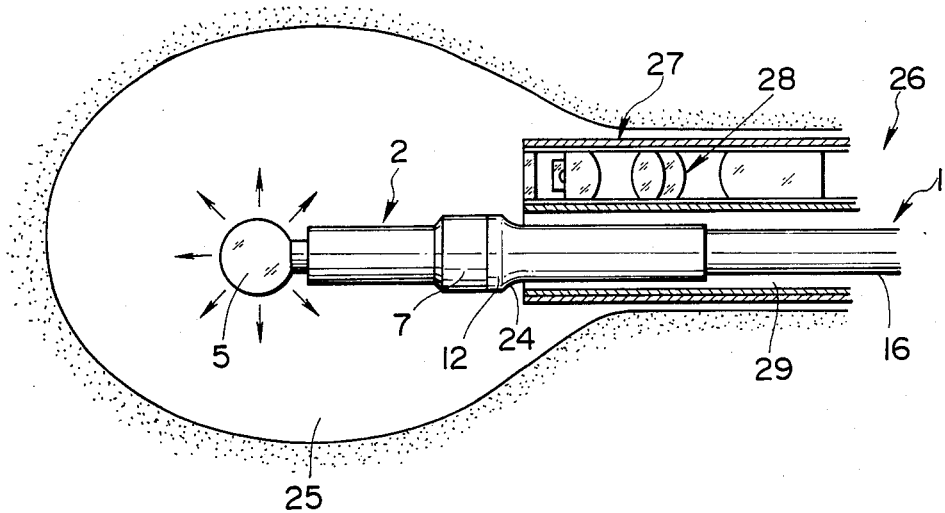
FIG. 3 is a sectioned view of the second embodiment of the present invention.

FIG. 3 shows a sectioned view of the second embodiment of the present invention. In this embodiment, the laser probe 1 of the same formation as of the above described first embodiment is used in an endoscope 26 which may be either hard or soft. This endoscope 26 comprises a gripping and operating part on the hand gripping side, an inserted part and a tip forming part 27 and has an illuminating optical system not illustrated and observing optical system 28 so that the body cavity 25 in which the endoscope is inserted may be observed. This endoscope 26 has a probe channel 29 leading to the end surface of the tip forming part 27 through the inserted part from the operating part and the laser probe 1 of the present invention is inserted into the body cavity 25 through this probe channel 29. In the embodiment by this endoscope, the cure is possible under the endoscope observation, the position of the light diffusing part 5 and the laser light radiating state can be always watched and the cure can be made safely and positively.

FIG. 4 shows a sectioned view of the third embodiment of the present invention.

In this embodiment, the light diffusing part 5 is fitted to the tip of the probe channel 29. That is to say, the above mentioned spherical hollow light diffusing part 5 is secured in the neck part to a holding member 32 having a male screw 31 on the outer periphery and, on the other hand, the tip part of the probe channel 29 formed through a tip mouthpiece 33 of the endoscope 26 is formed to be a recess and the male screw 31 of the above mentioned holding member 32 is screwed with the female screw 34 to fit the holding member 32. By the way, the light leading fibers 15 are the same as in the first embodiment and are inserted through the probe channel 29. The other formations and operations are the same as in the first and second embodiments.

FIGS. 5(A), (B) and (C) show the fourth embodiment of the present invention.

In this embodiment, in the spherical hollow light diffusing part 5 forming the tip of the laser probe 1, in order to regulate the laser light emitting direction, planes 35a, 35b and 35c emitting no laser light are formed and are reflection-coated to reflect a laser light.

In this embodiment, as the laser light emitting direction can be regulated, by selectively using the light diffusing part 5 having the plane in a position different in response to the use, using position and distributed state of generations of tumors, the laser light can be radiated efficiently.

It is apparent that working manners different in a wide range can be formed on the basis of the present invention without deviating from the spirit and scope of the invention. This invention is not restricted by the specific working manner except being limited by the appended claims.

We claim:

1. A laser probe endoscope comprising:
   a handle;
   a hollow shaft body affixed to said handle;
   a cylindrical neck part extending from said hollow shaft body;
   at least one light-leading fiber passing through said handle, said shaft body and said neck part and terminating beyond said neck part;
   a light diffusing tip disposed around the distal end of said light-leading fiber, said tip being hollow, rigid, transparent, and substantially spherical;
   a light-dispersing medium within said hollow sphere, said medium comprising a transparent liquid in which is suspended a fine particulate material; and
   a laser light source disposed at the end of said light-leading fiber proximal to said handle,
   wherein laser light is transmitted through said light-leading fiber to said light diffusing tip and wherein said light-dispersing medium diffuses said laser light in a wide range with a uniform intensity.

2. A laser probe according to claim 1 wherein a planar portion regulating the laser light emitting direction is formed in a part of said substantially spherical hollow light diffusing part.

3. A laser probe according to claim 2 wherein said planar portion formed in a part of said substantially spherical hollow light diffusing part is reflection-coated to reflect the laser light.

4. A laser probe endoscope according to claim 1, further comprising an illuminating system and an optical fiber viewing system.

* * * * *